United States Patent [19]

Trouve

[11] Patent Number: 5,393,333
[45] Date of Patent: Feb. 28, 1995

[54] FILM-FORMING PRODUCT FOR COATING SOLID FORMS, PROCESS FOR ITS MANUFACTURE AND PRODUCTS COATED WITH THIS FILM-FORMING PRODUCT

[75] Inventor: Gérard Trouve, Castres, France

[73] Assignee: Societe Anonyme Societe D'Exploitation De Produits Pour Les Industries Chimiques S.E.P.P.I.C., Cedex, France

[21] Appl. No.: 927,516

[22] PCT Filed: Mar. 22, 1991

[86] PCT No.: PCT/FR91/00232

§ 371 Date: Sep. 16, 1992

§ 102(e) Date: Sep. 16, 1992

[87] PCT Pub. No.: WO91/14729

PCT Pub. Date: Oct. 3, 1991

[30] Foreign Application Priority Data

Mar. 27, 1990 [FR] France ............... 90 03915

[51] Int. Cl.⁶ ............... C09D 101/00; C09D 105/00; A61K 9/14; A61K 9/30
[52] U.S. Cl. ............... 106/149; 424/439; 424/442; 424/475; 424/476; 424/477; 424/480; 424/482; 424/489; 424/490; 424/491; 424/493; 424/494; 424/497; 424/499; 424/501; 424/502; 426/96; 427/212; 523/100; 523/105
[58] Field of Search ............... 106/124, 149, 156, 153, 106/159, 161, 163.1, 169, 170, 171, 178, 183, 189, 197.1, 198, 199, 203, 204, 162, 210, 211, 213, 214, 215, 217, 243; 424/439, 440, 442, 464, 475–477, 480, 482, 489–491, 493–494, 497–499, 501–502; 426/96; 427/3, 212; 523/100, 105

[56] References Cited

U.S. PATENT DOCUMENTS

4,543,370  9/1985  Porter et al. ............... 523/100
4,556,552  12/1985  Porter et al. ............... 427/3
4,683,256  7/1987  Porter et al. ............... 524/285
4,704,295  11/1987  Porter et al. ............... 427/3
4,816,298  3/1989  Alderman et al. ............... 427/212

FOREIGN PATENT DOCUMENTS

0318314  5/1989  European Pat. Off. .
2548675  1/1985  France .
2065691  7/1981  United Kingdom .
8501207  3/1985  WIPO .

OTHER PUBLICATIONS

US Pharmacopoeia, "Powder Fineness", p. 811 & "Pharmaceutic Ingredients", pp. 1857–1859, [No date].
European Pharmacopoeia, "Granules", pp. 694–695, [No date].
Kirk-Othmer, "Encyclopedia Of Chemical Technology", Third Edition, vol. 17, pp. 871–878, [No date].
Banque de Donnees wpil, Abstract No. 86-090761 Derwent Publications Ltd., London, GB. for JP-A-61 036206 (Kanebo KKK), Feb. 20, 1986.

Primary Examiner—Anthony Green
Attorney, Agent, or Firm—Ladas & Parry

[57] ABSTRACT

The present invention relates to a film-forming product for coating solid forms, to a process for the manufacture of this film-forming product and to products coated with this film-forming product. According to the invention, this film-forming product takes the form of homogeneous granular particles which can easily be dispersed in an aqueous or organic solvent and which make it possible to obtain a uniform non-matt film, and its dry matter comprises:

- at least one ingestible, non-toxic film-forming substance in an amount of between 30 and 95% by weight;
- at least one colored pigment in an amount of between 5 and 50% by weight; and
- if appropriate, at least one edible plasticizer in an amount less than or equal to 30% by weight.

24 Claims, No Drawings

FILM-FORMING PRODUCT FOR COATING SOLID FORMS, PROCESS FOR ITS MANUFACTURE AND PRODUCTS COATED WITH THIS FILM-FORMING PRODUCT

The present invention relates in general terms to a novel film-forming product for coating solid forms, preferably of agricultural, pharmaceutical or food products, to the process for its preparation and to products coated with this film-forming product.

Numerous film-forming products are known for coating solid forms of pharmaceutical or food products. These film-forming products differ essentially in their composition and in the form which they take.

In general, these products contain cellulosic polymers, colored pigments, plasticizers and, if appropriate, various fillers.

French patent no. 2.470.598 describes a product which contains these different ingredients and which takes the form of a dry solvent-free mixture. This product can easily be dispersed in organic or aqueous solvents to give a film-forming solution capable of being sprayed on to the products to be coated, but has the disadvantage of generating soiling colored dusts when it is handled or transferred.

Moreover, this product is not free-flowing and, because of the substantial differences in the morphology and particle size of its various constituents, undesirable variations are observed in the colors of the coating.

U.S. Pat. No. 4,816,298 describes a process for the film-coating of tablets, comprising the preparation of particles consisting of hot-melt polymer, plasticizer and colored pigment.

These particles, which have a diameter of between about 1 and about 0.1 mm, do not cause dust, are stable and are easily dispersed in cold water.

However, this process requires the use of very considerable amounts (more than 30% by weight) of plasticizer in order to "solubilize" the polymer and obtain a melting/extrusion point which is not excessive. Moreover, in the Examples indicated in said document, the extrusion is carried out at a temperature of the order of 90° C., which can damage the colorants or lakes required for coloring the films.

French patent 2.548.675 in the name of the Applicant describes a film-forming product which contains α-cellulose and which takes the form of nonpulverulent granules with a diameter of about 0.5 to 1 mm, in which the different constituents are homogeneously distributed.

The product thus obtained can very easily be dispersed and entails no risk of stratification.

Furthermore, for the same viscosity, the coating solutions obtained from this product are more concentrated than those obtained from the products described in French patent 2.470.598 and U.S. Pat. No. 4,816,298 and permit more rapid coating of the products to be coated.

However, the films obtained from such a product have a matt appearance and cannot easily be made shiny.

It is important to note that α-cellulose is considered and presented as an essential constituent for the production of granules because of its role as a binder and because it also ensures that the coating film adheres well to the product to be coated.

The present invention is based on the observation that the presence of α-cellulose in the granules produced according to French patent 2.548.675 results in a film with a relatively non-uniform surface which does not make it possible to give said film a shiny appearance.

The invention is based secondly on the discovery of the fact that it is possible to prepare a film-forming product, free of α-cellulose, in the form of granular particles which enable uniform non-matt films to be obtained.

The object of the present invention is therefore to solve the technical problem of providing a novel film-forming product consisting of granular particles which can easily be dispersed in an aqueous or organic solvent and which make it possible to obtain a uniform film capable of being made shiny.

The solution to this technical problem, according to the present invention, consists of a film-forming product, free of α-cellulose, for coating solid forms, said product taking the form of homogeneous granular particles which can easily be dispersed in an aqueous or organic solvent and which make it possible to obtain a uniform non-matt film, and its dry matter comprising:

- at least one ingestible, non-toxic film-forming substance in an amount of between 30 and 95% by weight;
- if appropriate, at least one colored pigment in an amount of between 5 and 50% by weight; and
- if appropriate, at least one edible plasticizer in an amount less than or equal to 30% by weight.

Advantageously, the above-mentioned dry matter comprises:

- 60 to 80% by weight, and preferably about 65 to about 75% by weight, of film-forming substance;
- 10 to 40% by weight, and preferably about 15 to about 35% by weight, of colored pigment; and
- 0 to 25% by weight, preferably about 5 to about 15% and particularly preferably 10% by weight, of plasticizer.

According to one particular characteristic, the film-forming product according to the invention also comprises at least one filler selected from an opacifier, a water repellent or else a wetting agent.

The film-forming substance used in the product according to the invention can consist of one or more known ingestible film-forming agents described previously, for example in the above-mentioned patents.

Among these products, the following may be mentioned more especially as cellulose derivatives which can be used: cellulose alkyl ethers or alkyl esters such as, for example, methyl cellulose, hydroxypropyl cellulose, hydroxypropyl methyl cellulose, cellulose acetophthalate, cellulose acetate or ethyl cellulose; polyvinylpyrrolidone; zein; and acrylic polymers.

It will be advantageous to use a hydroxypropyl methyl cellulose with a viscosity of between 3 and 15 cP at room temperature as a 2% by weight solution in water.

The colored pigments which can be used according to the invention can be selected from the pigments used hitherto in the manufacture of film-forming products for the coating of solid forms of pharmaceutical or food products.

Examples of these pigments are described in particular in the above-mentioned patents.

Among these pigments, any food-grade pigments or colorants (soluble or in the form of lakes) will be used, especially titanium dioxide.

The plasticizers which can make up part of the film-forming product according to the invention can be selected from the known plasticizers described especially in the above-mentioned patents. Examples which may be mentioned of plasticizers which can be used are glycerol, polyethylene glycol with a molecular weight of between 400 and 10,000, glycerol (sic), propylene glycol, sugars, especially glucose, maltodextrins, acetylated monoglycerides, citric or lactic acid esters and ethoxylated fatty acids.

The film-forming product according to the invention can also contain at least one filler normally used for modifying the properties of the coating material and the protection of said material. Examples of fillers which may be mentioned are opacifiers such as, for example, talc, water repellents such as, for example, fatty acids and derivatives thereof, silicone polymers and wetting agents such as, for example, the traditional edible surfactants.

According to a second feature, the present invention relates to a process for the preparation of a film-forming product in the form of granular particles, such as defined above, which comprises wetting at least a major part, greater than about 95% by weight of the total weight, of the pulverulent film-forming substance with a binding granulating solution in a mixing-granulating device or in a fluidized air bed.

If the wetting is carried out in a fluidized air bed, the granular particles are obtained directly.

The devices known under the name Glatt or Aeromatic may be mentioned as examples of fluidized air bed devices which can be used.

If the above-mentioned wetting is carried out in a mixer-granulator, the moist mass obtained is subsequently ground and then dried and, if appropriate, sieved to give homogeneous granular particles. The devices known under the name Diosna or Lodige may be mentioned as examples of mixing-granulating devices which can be used.

According to one particular characteristic of the process according to the invention, the above-mentioned binding granulating solution comprises:
all the colored pigments;
a small part, of between about 0.01 and about 5% by weight of the total weight, of the film-forming substance; and
if appropriate, the plasticizer, in a solvent such as, preferably, water.

The dispersion of a small part of the film-forming agent in the granulation binder makes it possible to obtain a binding solution which is more homogeneous and more stable with time and which does not need to be agitated during the granulation operation. This dispersion also makes it possible to increase the binding power of the solution compared with a simple dispersion of pigment in the solvent. In fact, it has been observed that the perfectly hydrated film-forming agent can wet and coat the pigment particles and thus favor the formation of homogeneous granules when mixed with the powders.

Thus the dispersion of a small part of the film-forming agent in the granulation binder makes it possible to prepare granules free of α-cellulose.

According to another particular characteristic of the process according to the invention, the above-mentioned binding granulating solution is obtained by mixing a "stock" dispersion containing a part, of between about 10 and about 50% of the total weight, of the solvent, the colored pigments and the above-mentioned small part of the film-forming agent with a dispersion containing the remainder of the solvent and, if appropriate, the plasticizer.

Advantageously, prior to the mixing of these two dispersions, the "stock" dispersion is ground, preferably in a ball mill, to give a fine and homogeneous particle size, for example below 150 μm.

According to a third feature, the invention relates to products which have been coated with a film-forming product such as defined above. Said coated products are preferably for use in agriculture, foodstuffs or pharmacy.

This coating can be effected by dispersing the film-forming product in an appropriate organic or aqueous solvent to give a film-forming solution, and by spraying this solution in a manner known per se on to the products to be coated.

The invention will be understood more clearly with the aid of the following illustrative Examples, which are given without implying a limitation.

EXAMPLE 1

A film-forming product according to the invention, in the form of granular particles without plasticizer, was prepared in the following manner.

3.5 kg of food-grade titanium dioxide (anatase) are dispersed in 4.6 kg of an aqueous solution containing 0.13 kg of hydroxypropyl methyl cellulose (6 cPs).

This dispersion is ground to give a homogeneous milk free of solid agglomerate.

This milk is introduced gradually into a Diosna V100 mixer-granulator containing 6.4 kg of hydroxypropyl methyl cellulose (6 cPs).

The speed of the mixer is kept at level 1 for 3 min.

0.2 kg of water is then added to give more homogeneous grains, the speed of the mixer being kept at level 2 for a further 1 min.

The moist grains thus obtained are then introduced into a mill of the Tornado type, equipped with a 5 mm grid and rotating at minimum speed. The product thus obtained is then dried in a ventilated oven at 110° C. for 22 h.

This gives a white granular powder containing about 1% of water.

The characteristics of the product obtained have been collated in Table I.

The corresponding measurements and analyses were performed in the following manner:
run-out time
This corresponds to the time required for 100 g of granules, placed in a standardized funnel (NF 35 032), to run out totally without the aid of vibration or shock.
dissolution time
In a 1 l beaker of diameter 220 mm, a dispersion of 75 g of film-forming granules in 425 g of deionized water at 20° C. is prepared by agitation with a Raynerie deflocculating turbine of diameter 65 mm, rotating at 1500 rpm.

The dissolution time is the time required for all the particles or grains visible to the naked eye to disappear.
viscosity
The dispersion prepared above is agitated for 1 h.

This dispersion is then left to stand for 1 h and its viscosity at 20° C. is measured by means of a Brookfield viscometer (model LVT) equipped with a no. 2 spindle rotating at a speed of 60 rpm.
stability
About 10 ml of the solution described above, the viscosity of which has been measured, are placed in a centrifuge rotating at 3000 rpm and producing an acceleration of 1500 g.

The volume of the centrifugation residue $V_c$ and that of the supernatant $V_s$ (expressed as percentages) are noted after 15 min of centrifugation.

Preparation of Coated Tablets 500 g of tablets are placed in an Erweka coating turbine rotating at 18 rpm.

A 15% solution of the granules is prepared as indicated above and sprayed with a Binks gun at a rate of 10 g/min.

Warm air at about 40° C. is blown into the turbine.

After about 100 g of solution have been deposited, the tablets are removed from the turbine. They are perfectly covered with a uniform white film free of roughnesses and of shiny appearance.

The characteristics of two commercially available film-forming products were measured by way of comparison.

The product Opadry YS 7802 from Colorcon is a dry solvent-free mixture according to French patent 2.470.598.

The Applicant's product Sépifilm 752 is a granular powder prepared according to French patent 2.548.695.

The results are indicated in Table I, which also mentions the appearance of the film obtained with these products by following the protocol described above.

TABLE I

|  | Film-forming product of Example 1 | OPADRY YS 7802 | SEPIFILM 752 |
| --- | --- | --- | --- |
| Run-out time (s) | 12 | does not run out | 11 |
| Dissolution time (min) | 14 | 6 (with lumps) | 9 (without lumps) |
| Viscosity (mPa.s) of 154 solution | 500 | 275 | 200 |
| Stability of 15% solution | $V_s = 6.7\%$ $V_c = 0$ | $V_s = 11\%$ $V_c = 0$ | $V_s = 19\%$ $V_c = 20\%$ |
| Appearance of the film | white, uniform, shiny | white, uniform, shiny | white, matt |

EXAMPLE 2

A dispersion is prepared by agitating a mixture containing 3.5 kg of titanium dioxide (anatase) and 0.16 kg of HPMC (3 cPs) in 3.5 kg of demineralized water.

This dispersion is finely ground and then poured, by means of a peristaltic pump with an output of 1.75 kg/min, into a Diosna V100 mixer-granulator containing 3.9 kg of HPMC (6 cPs) and 2.4 kg of HPMC (3 cPs). The operating conditions are the same as those described in Example 1.

Granular particles having the characteristics shown in Table II are obtained after sieving on a 2 mm grid.

Tablets were coated with these granular particles in the same way as in Example 1 and the film obtained is uniform, white and shiny.

EXAMPLE 3

A. Preparation of a Granulation Binder 0.75 kg of magnesium oxide and 0.075 kg of HPMC (3 cPs) are dispersed in 2 kg of demineralized water.

This "stock" dispersion is ground.

This ground stock dispersion is mixed with a dispersion consisting of 1.675 kg of propylene glycol (plasticizer) in 0.5 kg of water.

B. Preparation of the Granular Particles

The granulation binder obtained in step A is sufficiently stable and homogeneous to be introduced by means of a pump into a Diosna V100 mixer-granulator containing 5 kg of HPMC (3 cPs).

The granulation conditions are identical to those described in Example 1. However, a quantity of finishing water is added to give a moist granular mass of perfectly homogeneous appearance. This mass is dried and ground to give granules having the characteristics collated in Table II.

EXAMPLE 4

Step A: Preparation of a Binding Granulating Solution

A "stock" dispersion containing 2.94 kg of titanium dioxide in 2.5 kg of demineralized water is prepared.

This dispersion is ground in a ball mill.

A second dispersion of 0.20 kg of HPMC (6 cPs) in 0.5 kg of hot water, to which 0.91 kg of triacetin is added, is prepared separately.

The stock dispersion is poured into the second dispersion, with agitation, to give a stable granulation binder.

Step B: Preparation of Granular Particles

The binder obtained in step A is introduced over 5 min, by means of a peristaltic pump, on to 5.95 kg of HPMC (3 cPs) placed in a Diosna V100 mixer rotating at speed 1.

Finishing water is added in a sufficient quantity to give a homogeneous mass, the mixer then rotating at speed 2 for a further 1 min. After grinding, drying and sieving as indicated in Example 1, the granules obtained have the characteristics indicated in Table II and a dry extract of 95%.

EXAMPLE 5

Colored film-forming granules are prepared in this Example.

Step A: Preparation of a Granulation Binder

A dispersion of:
1.771 kg of titanium dioxide;
0.018 kg of yellow iron oxide;
0.065 kg of black iron oxide; and
0.045 kg of indigotin in the form of aluminum lake, in 1.8 kg of water, is prepared.

This "stock" dispersion is ground.

A second dispersion consisting of 0.8 kg of polyethylene glycol 400, 0.1 kg of HPMC (6 cPs) and 0.9 kg of demineralized water is prepared.

The "stock" dispersion is mixed into this second dispersion.

Step B: Preparation of Granules

The solution obtained in step A is introduced over 10 min, by means of a peristaltic pump, into a mixer-granulator containing 7.3 kg of HPMC (6 cPs). The mixture is kept for a few minutes at speed 1.

0.3 kg of demineralized water is then introduced to give a homogeneous mass and agitation is continued for a further 6 min at speed 1.

The moist mass thus obtained is dried, ground and sieved as described in Example 1 to give green granular particles whose dry matter represents 97% by weight and whose characteristics are collated in Table II.

Complementary experiments were carried out with other film-forming substances, pigments and plasticizers in variable proportions, making it possible to determine the general parameters, indicated above, which influence the preparation of granular particles according to the invention.

TABLE II

|  | Film-forming product of Example 2 | Film-forming product of Example 3 | Film-forming product of Example 4 | Film-forming product of Example 5 |
|---|---|---|---|---|
| Run-out time (s) | 17 | 14 | 20 |  |
| Dissolution time (min) | 17 | — | 14 |  |
| Viscosity (mPa.s) of 15% solution | 280 | 470 | 275 |  |
| Stability of 15% solution | $V_s = 6.7\%$  $V_c = 0$ | — | $V_s = 2.7\%$  $V_c = 0$ |  |
| Appearance of the film | uniform, white, shiny | thin, uniform, opaque | uniform white, shiny |  |

What is claimed is:

1. In a film-forming product for coating a solid form wherein the product has a dry matter comprising a film-forming non-toxic edible substance, an edible colorant and an edible plasticizer and is dispersible in an aqueous or organic solvent whereupon it can be used to coat said solid form, the improvement wherein the dry matter of the product (a) is free of α-cellulose and comprises said edible, non-toxic film-forming substance in an amount of between 30 and 95% by weight; said edible colorant in an amount up to 50% by weight; and said edible plasticizer in an amount up to 30% by weight, and (b) has the form of homogeneous granular particles such that, when dispersed in said aqueous or organic solvent, the product can be used to coat said solid form with a uniform non-matte film.

2. A film-forming product as claimed in claim 1 wherein said film-forming substance is selected from the group consisting of cellulose alkyl ethers, cellulose alkyl esters, polyvinylpyrrolidone, zein and acrylic polymers, and said edible plasticizer is selected from the group consisting of glycerol, polyethylene glycol with a molecular weight of between 400 and 10,000, propylene glycol, sugars, maltodextrins, acetylated monoglycerides, citric acid esters, lactic acid esters and ethoxylated fatty acids.

3. A film-forming product as claimed in claim 2 wherein said colorant is selected from the group consisting of titanium dioxide, iron oxide, and indigotin.

4. A film-forming product as claimed in claim 1, wherein said non-toxic film-forming substance is selected from the group consisting of cellulose alkyl ethers, cellulose alkyl esters, polyvinylpyrrolidone, zein and acrylic polymers in an amount of between 65 and 75% by weight; said colorant is selected from the group consisting of titanium dioxide, iron oxide, and indigotin in an amount of between 15 and 35% by weight; and said edible plasticizer is selected from the group consisting of glycerol, polyethylene glycol with a molecular weight of between 400 and 10,000, propylene glycol, sugars, maltodextrins, acetylated monoglycerides, citric acid esters, lactic acid esters and ethoxylated fatty acids in an amount of between 5 and 15% by weight.

5. A film-forming product according to claim 1, wherein said dry matter comprises:
   60 to 80% by weight of film-forming substance;
   up to 40% by weight of colorant; and
   up to 25% by weight of plasticizer.

6. A film-forming product according to claim 1, wherein said dry matter comprises:
   65 to 75% by weight of film-forming substance;
   15 to 35% by weight of colorant; and
   5 to 15% by weight of plasticizer.

7. A film-forming product according to claim 1, wherein said dry matter further comprises at least one filler selected from the group consisting of opacifiers, water repellents and wetting agents.

8. A film-forming product according to claim 1, wherein said film-forming substance is a hydroxypropyl methyl cellulose.

9. A coated product for use in agriculture, foodstuffs or pharmacy, which has been coated with a film-forming product as defined in claim 1.

10. In a process for preparing a dry edible film coating composition which can be constituted with a solvent to form a dispersion for coating a solid form, wherein a film forming non-toxic edible substance is combined with an edible colorant and an edible plasticizer so that the composition contains dry matter which contains said film forming substance, said colorant and said plasticizer, the improvement comprising forming said composition so that the dry matter is free of a-cellulose and contains the film-forming substance in a total amount of between about 30–95% by weight, the colorant in an amount of up to about 50% by weight, and the plasticizer in an amount of up to about 30% by weight by a process comprising the following steps: (a) preparing an aqueous dispersion comprising said colorant, said plasticizer and a first portion of said film forming substance, with said first portion comprising between about 0.01 and 5% by weight of the total amount of the film forming substance; (b) mixing the aqueous dispersion with a second portion of the film forming substance in a mixer-granulator to form a moist mass, with said second portion comprising between about 95 and 99.99% by weight of the total amount of the film forming substance; and (c) grinding, drying and, if necessary, sieving the moist mass to obtain homogeneous granular particles which can be dispersed in an aqueous or organic solvent to form a dispersion which can be used to coat the solid form with a uniform non-matte film.

11. A process according to claim 10, wherein prior to said mixing step (b), the aqueous dispersion is ground to give a fine and homogeneous particle size.

12. A process as claimed in claim 10, wherein said film-forming substance is selected from the group consisting of cellulose alkyl ethers, cellulose alkyl esters, polyvinylpyrrolidone, zein and acrylic polymers; and said edible plasticizer is selected from the group consisting of glycerol, polyethylene glycol with a molecular weight of between 400 and 10,000, propylene glycol, sugars, maltodextrins, acetylated monoglycerides, citric acid esters, lactic acid esters and ethoxylated fatty acids.

13. A process as claimed in claim 12, wherein said colorant is selected from the group consisting of titanium dioxide, iron oxide, and indigotin.

14. A process as claimed in claim 13, wherein the film-forming substance is present in said dry matter in a total amount of between about 65 and 75% by weight; the edible colorant is present in the dry matter in an amount of between about 15 and 35% by weight; and the edible plasticizer is present in the dry matter in an amount of between about 5 and 15% by weight.

15. A process according to claim 10, wherein said aqueous dispersion is prepared by mixing a first dispersion containing 10 to 50% of the total weight of an aqueous solvent said edible colorant in its entirety and between 0.01 and 5% of the total amount of said film-forming substance with a second dispersion containing 50 to 90% of the total weight of the aqueous solvent and said plasticizer in its entirety.

16. A process according to claim 12, wherein said aqueous dispersion is prepared by mixing a first dispersion containing 10 to 50% of the total weight of an aqueous solvent said edible colorant in its entirety and between 0.01 and 5% of the total amount of said film-forming substance with a second dispersion containing 50 to 90% of the total weight of the aqueous solvent and said plasticizer in its entirety.

17. A process according to claim 14, wherein said aqueous dispersion is prepared by mixing a first dispersion containing 10 to 50% of the total weight of an aqueous solvent said edible colorant in its entirety and between 0.01 and 5% of the total amount of said film-forming substance with a second dispersion containing 50 to 90% of the total weight of the aqueous solvent and said plasticizer in its entirety.

18. In a process for preparing a dry edible film coating composition which can be constituted with a solvent to form a dispersion for coating a solid form, wherein a dry film forming non-toxic edible substance is combined with an edible colorant and an edible plasticizer so that the composition contains dry matter which comprises said film forming substance, said colorant and said plasticizer, the improvement comprising forming said composition so that the dry matter is free of α-cellulose and contains the film-forming substance in a total amount of between about 30–95% by weight, the colorant in an amount of up to about 50% by weight, and the plasticizer in an amount of up to about 30% by weight by a process comprising the following steps: (a) preparing an aqueous dispersion comprising said colorant, said plasticizer and a first portion of said film forming substance, with said first portion comprising between about 0.01 and 5% by weight of the total amount of the film forming substance; (b) mixing the aqueous dispersion with a second portion of the film forming substance in a fluidized air bed, with said second portion comprising between about 95 and 99.99% by weight of the total amount of the film forming substance, whereby to obtain homogeneous granular particles which can be dispersed in an aqueous or organic solvent to form a dispersion which can be used to coat the said form with a non-uniform matte film.

19. A process as claimed in claim 18, wherein said film-forming substance is selected from the group consisting of cellulose alkyl ethers, cellulose alkyl esters, polyvinylpyrrolidone, zein and acrylic polymers; and said edible plasticizer is selected from the group consisting of glycerol, polyethylene glycol with a molecular weight of between 400 and 10,000, propylene glycol, sugars, maltodextrins, acetylated monoglycerides, citric acid esters, lactic acid esters and ethoxylated fatty acids.

20. A process as claimed in claim 9, wherein said colorant is selected from the group consisting of titanium dioxide, iron oxide, and indigotin.

21. A process as claimed in claim 20, wherein the film-forming substance is present in said dry matter in a total amount of between about 65 and 75% by weight; the edible colorant is present in the dry matter in an amount of between about 15 and 35% by weight; and the edible plasticizer is present in the dry matter in an amount of between about 5 and 15% by weight.

22. A process according to claim 18, wherein said aqueous dispersion is prepared by mixing a first dispersion containing 10 to 50% of the total weight of an aqueous solvent said edible colorant in its entirety and between 0.01 and 5% of the total amount of said film-forming substance with a second dispersion containing 50 to 90% of the total weight of the aqueous solvent and said plasticizer in its entirety.

23. A process according to claim 19, wherein said aqueous dispersion is prepared by mixing a first dispersion containing 10 to 50% of the total weight of an aqueous solvent said edible colorant in its entirety and between 0.01 and 5% of the total amount of said film-forming substance with a second dispersion containing 50 to 90% of the total weight of the aqueous solvent and said plasticizer in its entirety.

24. A process according to claim 21, wherein said aqueous dispersion is prepared by mixing a first dispersion containing 10 to 50% of the total weight of an aqueous solvent said edible colorant in its entirety and between 0.01 and 5% of the total amount of said film-forming substance with a second dispersion containing 50 to 90% of the total weight of the aqueous solvent and said plasticizer in its entirety.

* * * * *